United States Patent [19]
van den Bosch

[11] Patent Number: 6,017,515
[45] Date of Patent: Jan. 25, 2000

[54] METHOD FOR PREPARING A PREPARATION FOR BLEACHING TEETH OR FOR TREATING SKIN COMPLAINTS AND MUCOUS MEMBRANE DISORDERS

[75] Inventor: Willem Frederik van den Bosch, Oegstgeest, Netherlands

[73] Assignee: Diamond White A.V.V., Aruba, Netherlands Antilles

[21] Appl. No.: 08/894,636

[22] PCT Filed: Feb. 23, 1996

[86] PCT No.: PCT/NL96/00091

§ 371 Date: Sep. 5, 1997

§ 102(e) Date: Sep. 5, 1997

[87] PCT Pub. No.: WO96/25916

PCT Pub. Date: Aug. 29, 1996

[30] Foreign Application Priority Data

Feb. 24, 1995 [NL] Netherlands ............... 9500373

[51] Int. Cl.$^7$ ............... A61K 7/16; A61K 7/20; A61K 33/22; A61K 33/40
[52] U.S. Cl. ............... 424/53; 424/62; 424/613; 424/660; 433/215; 433/216
[58] Field of Search ............... 424/53, 62, 613, 424/660; 433/215, 216

[56] References Cited

U.S. PATENT DOCUMENTS

| | | | |
|---|---|---|---|
| 1,435,498 | 11/1922 | Resnick | 424/53 |
| 3,372,125 | 3/1968 | Hill | 252/99 |
| 3,574,824 | 4/1971 | Echeandia et al. | 424/50 |
| 3,793,211 | 2/1974 | Kohlhepp et al. | |
| 3,886,266 | 5/1975 | Goldman et al. | 424/53 |
| 3,936,385 | 2/1976 | Cheng | 252/99 |
| 3,988,433 | 10/1976 | Benedict | 424/53 |
| 4,060,600 | 11/1977 | Vit | 424/53 |
| 4,490,269 | 12/1984 | Gallopo | 252/94 |
| 4,552,679 | 11/1985 | Schobel et al. | 252/99 |
| 5,032,178 | 7/1991 | Cornell | 424/53 |
| 5,041,280 | 8/1991 | Smigel | 424/53 |
| 5,122,365 | 6/1992 | Murayama | 424/53 |
| 5,165,424 | 11/1992 | Silverman | 433/216 |
| 5,217,710 | 6/1993 | Williams et al. | 424/33 |
| 5,240,415 | 8/1993 | Haynie | 424/53 |
| 5,264,205 | 11/1993 | Kelly | 424/53 |
| 5,279,816 | 1/1994 | Church et al. | 424/53 |
| 5,302,375 | 4/1994 | Viscio | 424/53 |
| 5,372,802 | 12/1994 | Barrows et al. | 424/53 |
| 5,372,803 | 12/1994 | Williams et al. | 424/53 |
| 5,374,368 | 12/1994 | Hauschild | 424/53 |
| 5,616,313 | 4/1997 | Williams et al. | 424/53 |
| 5,632,972 | 5/1997 | Williams et al. | 424/53 |
| 5,645,428 | 7/1997 | Yarborough | 433/215 |
| 5,648,064 | 7/1997 | Gaffar et al. | 424/53 |
| 5,713,738 | 2/1998 | Yarborough | 433/215 |

FOREIGN PATENT DOCUMENTS

| | | | |
|---|---|---|---|
| 1041101 | 4/1990 | China . | |
| 0 081 962 | 6/1983 | European Pat. Off. . | |
| 0 085 891 B1 | 10/1986 | European Pat. Off. | 424/53 |
| 0 360 299 | 3/1990 | European Pat. Off. . | |
| 0 451 105 | 10/1991 | European Pat. Off. . | |
| 404 344 | 11/1909 | France . | |
| 2 239 987 | 3/1975 | France . | |
| 552 803 | 4/1943 | United Kingdom . | |
| 1 469 398 | 4/1977 | United Kingdom . | |
| 2 289 841 | 12/1995 | United Kingdom | 424/53 |
| 2 290 233 | 12/1995 | United Kingdom | 424/53 |
| WO 84/03274 | 8/1984 | WIPO . | |
| 96/13245 | 5/1996 | WIPO | 424/49 |
| 96/25916 | 8/1996 | WIPO | 424/53 |
| 98/04235 | 2/1998 | WIPO | 424/53 |

*Primary Examiner*—Shep K. Rose
*Attorney, Agent, or Firm*—Young & Thompson

[57] ABSTRACT

The present invention relates to a method for preparing a preparation for bleaching teeth or for treating skin complaints and mucous membrane disorders, in which method at least the following are combined: (a) a gel or paste in which a component (i) is present, component (i) being composed of at least a cation $A^{n+}$ and an anion $O_mX^-$; where A is a metal from Group 1 or 2 of the periodic system, n=1 or 2, X is a halogen atom and m=1–4, and (b) a gel or paste in which a component (ii) is present, component (ii) being composed of at least a cation $A^{n+}$ and an anion $[B_pO_q]^{r-}$, where A is a metal from Group 1 or 2 of the periodic system, p=1–4, q=1–8 and r=1–3.

36 Claims, No Drawings

METHOD FOR PREPARING A PREPARATION FOR BLEACHING TEETH OR FOR TREATING SKIN COMPLAINTS AND MUCOUS MEMBRANE DISORDERS

This application is a 371 of PCT/NL96/00091 filed Feb. 23, 1996.

The present invention relates to a method for preparing a preparation for bleaching teeth or for treating skin complaints and mucous membrane disorders.

In cosmetic dentistry various products and techniques are used for bleaching both avital and vital teeth. Avital teeth are dead teeth which no longer contain a nerve or contain a nerve which is no longer functioning, for example as a result of a so-called root canal treatment. Vital teeth are live teeth and these do still contain a functioning nerve.

Bleaching of teeth can be carried out, for example, using the product Hi-Lite, which is marketed by Shofu Dental Corporation. This product contains concentrated hydrogen peroxide (35%) as active ingredient and is applied as such to the tooth to be bleached, after which it is allowed to act for 8–10 minutes. During this period bleaching of the tooth takes place as a result of so-called chemical activation.

Bleaching can be accelerated under the influence of light. In this case the tooth to which the product has been applied is irradiated using a special lamp, as a result of which the period which is needed for bleaching is shortened to 2–3 minutes. This latter method for bleaching teeth is described in more detail in an article by F. N. Hanosh and G. S. Hanosh in J. Esthet. Dent. 4 (1992) 90–95.

A significant disadvantage of the product Hi-Lite is that it contains the aggressive chemical substance hydrogen peroxide, which, moreover, is present in a high concentration (35%) in the product. The product therefore has to be handled very carefully. When handling this product contact with the skin must also be avoided and it is highly advisable to wear protective gloves and spectacles when handling this product. Furthermore, this product is not found to have a long-lasting bleaching action, that is to say the effect (durability) of the treatment clearly declines after a few months.

Other products, such as Nite-White, which is marketed by New Smile Care-Zahnkosmetik GmbH, contain carba-imide peroxide ($CO(NH_2)_2.H_2O_2$) as active constituent. According to the prior art, however, it is found that although an appreciable change in colour does occur after active treatment of the tooth to be bleached, this change in colour has virtually completely disappeared after only one week.

No effective agents are disclosed in the prior art for the treatment of skin complaints and mucous membrane disorders, in particular lesions.

The aim of the present invention is to provide a solution to the problems described above by the use of a preparation for bleaching teeth, the preparation containing no aggressive chemical substances. Another aim of the present invention is to provide an effective agent for the treatment of skin complaints and mucous membrane disorders, in particular lesions.

The present invention therefore relates to a method for preparing a preparation for. bleaching teeth or for treating skin complaints and mucous membrane disorders, in which method at least the following are combined:

(a) a gel or paste in which a component (i) is present, component (i) being composed of at least a cation $A^{n+}$ and an anion $O_mX^-$, where A is a metal from Group 1 or 2 of the periodic system, n=1 or 2, X is a halogen atom and m=1–4, and (b) a gel or paste in which a component (ii) is present, component (ii) being composed of at least a cation $A^{n+}$ and an anion $[B_pO_q]^{r-}$, where A is a metal from Group 1 or 2 of the periodic system, p=1–4, q=1–8 and r=1–3.

The term gel or paste is used to define materials which have a viscosity and flow characteristics which are comparable with those of a thick, optionally thixotropic, liquid. Examples of such materials are peanut butter, toothpaste, ointments and creams. In this description both terms gel and paste are used alongside one another, it being assumed that the two terms are synonyms of one another. In the formula $O_mX^-$ X can be fluorine, chlorine, bromine or iodine. Examples of the anion $O_mX^-$ are the hypochlorite, hypoiodite, chlorite, iodite, chlorate, bromate, Iodate, perchlorate and periodate anions.

Examples of the anion $[B_pO_q]^{r-}$ are perborate ($BO_3^-$), metaborate ($BO_2^-$), orthoborate ($BO_3^{3-}$), hypoborate ($B_2O_4^{2-}$) and pyroborate or tetraborate anions ($B_4O_7^{2-}$).

The preparation according to the invention can be obtained by combining constituents (a) and (b), the constituents (a) and (b) preferably being combined just before, for example 5 minutes to 1 hour before, or during the use of the preparation. In contrast, it is also possible to prepare the preparation longer in advance, for example 1 hour to 7 days beforehand, in which case, however, it is recommended that the preparation is stored at low temperature, preferably between 0° and 8° C., until such time as the preparation is used.

The constituents (a) and (b) can optionally contain further chemical or pharmaceutical substances or compounds, such as perfumes, aroma substances and flavourings, which are customarily used in dental preparations and products.

According to the invention, the preparation for bleaching teeth or for treating mucous membrane disorders is preferably prepared by combining constituents (a) and (b), component (i) being composed of at least a cation $A^{n+}$ and an anion $O_mX^-$, where A is lithium, sodium or potassium, n=1, X is a halogen atom and m=1, and component (ii) being composed of at least a cation $A^{n+}$ and an anion $[B_pO_q]^{r-}$, where A is lithium, sodium or potassium, p=1, q=2 or 3 and r=1. According to the invention, therefore, a hypohalite is used as component (i) and a borate as component (ii). Examples of a hypohalite are lithium hypochlorite, sodium hypochlorite, potassium hypoiodite and potassium hypochlorite. Examples of suitable borates are the perborates and metaborates of sodium, potassium and lithium.

According to the invention, A is in particular sodium and X chlorine and q=3 and r=1. Therefore, according to the invention component (i) is preferably a hypochlorite, in particular sodium hypochlorite, and component (ii) is a perborate, in particular sodium perborate.

Component (i) can contain one or more molecules of water as water of crystallisation. Preferably an aqueous solution of component (i) is used, for example a solution of sodium hypochlorite in water. Such a solution is also termed "bleaching water". Component (ii) can also contain one or more molecules of water as water of crystallisation, such as sodium perborate trihydrate and sodium perborate tetrahydrate. According to the invention all hydrates of both component (i) and component (ii) can be used and, therefore, all these hydrates fall within the scope of the invention.

Advantageously, constituents (a) and (b) also contain one or more additives, the additives preferably being one or more of the following components: (iii) a binder, (iv) a gelatinous thickener and (v) an agent which counteracts loss of moisture.

Suitable binders are glycerol, propylene glycol and certain gums, for example acacia gum, gum arabic, caraya gum, gum tragacanth and xanthan gum. According to the invention, component (iii) is in particular glycerol.

Suitable gelatinous thickeners are cellulose materials, for example cellulose, sodium carboxymethylcellulose, (hydroxy)propylcellulose, methylcellulose and ethylcellulose. According to the invention component (iv) is in particular sodium carboxymethylcellulose.

Suitable agents which counteract loss of moisture are alditols, for example erythritol, arabinitol, xylitol, galactitol, sorbitol, iditol, mannitol, heptitol and octitol. According to the invention, component (v) is in particular sorbitol.

According to the invention the sequence in which the components (i)–(v) are combined is important in order to obtain the preparation in the form of a homogenous gel or paste. According to the invention it is therefore important that homogenous constituents (a) and (b) are prepared. Constituent (a) is preferably prepared in accordance with the following steps:

1. mixing component (iii) and component (iv),
2. mixing the mixture obtained in step 1 with component (v), and
3. mixing the mixture obtained in step 2 with component (i).

Constituent (b) is preferably prepared in accordance with the following steps:

1. mixing component (iii) and component (iv),
2. mixing the mixture obtained in step 1 with component (v), and
3. mixing the mixture obtained in step 2 with component (ii).

According to the invention it is also possible to use other inorganic compounds which have a bleaching action instead of component (ii). Examples of such compounds are sodium percarbonate, sodium chlorite, sodium carbonate peroxyhydrate and sodium pyrophosphate peroxyhydrate.

The preparation is preferably prepared from a constituent (a) which comprises at least 0.1 to 95% by weight, preferably 1 to 50% by weight, of component (i) and from a constituent (b) which comprises at least 0.1 to 95% by weight, preferably 1 to 50% by weight, of component (ii).

More preferentially, the preparation is prepared from a constituent (a) which comprises at least
0.1 to 95% by weight, preferably 1 to 50% by weight, of component (i),
0.1 to 95% by weight, preferably 1 to 50% by weight, of component (iii),
0.01 to 20% by weight, preferably 0.1 to 10% by weight, of component (iv), and
0.1 to 95% by weight, preferably 1 to 50% by weight, of component (v),
and a constituent (b) which comprises at least
0.1 to 95% by weight, preferably 1 to 50% by weight, of component (ii)
0.1 to 95% by weight, preferably 1 to 50% by weight, of component (iii),
0.01 to 20% by weight, preferably 0.1 to 10% by weight, of component (iv), and
0.1 to 95% by weight, preferably 1 to 50% by weight, of component (v).

In particular, the preparation is prepared from a constituent (a) which comprises at least
0.1 to 95% by weight, preferably 1 to 50% by weight, of component (i),
0.1 to 95% by weight, preferably 1 to 50% by weight, of component (iii),
0.01 to 20% by weight, preferably 0.1 to 10% by weight, of component (iv), and
0.1 to 95% by weight, preferably 1 to 50% by weight, of component (v),
and optionally
0.1 to 20% by weight, preferably 1 to 15% by weight, of sodium citrate, and
0.01 to 5% by weight, preferably 0.1 to 0.4% by weight, of sodium fluoride,
and a constituent (b) which comprises at least
0.1 to 95% by weight, preferably 1 to 50% by weight, of component (ii)
0.1 to 95% by weight, preferably 1 to 50% by weight, of component (iii),
0.01 to 20% by weight, preferably 0.1 to 10% by weight, of component (iv), and
0.1 to 95% by weight, preferably 1 to 50% by weight, of component (v),
and optionally
0.1 to 50% by weight, preferably 1 to 20% by weight, of sodium citrate,
0.1 to 50% by weight, preferably 1 to 20% by weight, of magnesium sulphate and
0.1 to 50% by weight, preferably 1 to 20 by weight, of sodium sulphate.

A very particular embodiment of the present invention relates to a preparation of the composition indicated above, where component (iii) is glycerol, component (iv) is sodium carboxymethylcellulose and component (v) is sorbitol.

If desired, constituent (a) and constituent (b) can also comprise other chemical or pharmaceutical substances, for example perfumes, aroma substances and flavourings such as are generally used in dental products such as toothpastes, for example aspartame.

The particle size of the compounds in solid form is not critical, but these compounds are simpler to process to give a homogenous gel or paste if they are in finely divided form. An average particle size of 0.0001 to 1 mm, in particular 0.01 to 0.1 mm, is suitable. During mixing of the above-mentioned constituents, the mixture of said constituents can be heated briefly at a temperature of 50 to 150° C., preferably not higher than 100° C., in order to obtain homogeneous gels or pastes.

Constituent (b) can also contain other inorganic compounds which have a bleaching action, for example sodium percarbonate, sodium chlorite, sodium carbonate peroxyhydrate and sodium pyrophosphate peroxyhydrate, in addition to component (ii) or as a replacement for component (ii). Preferably, such a compound is used in an amount of 0.1 to 50% by weight, preferably 1 to 20% by weight and In particular in an amount of 5 to 10% by weight. If constituent (b) contains a compound other than component (ii), such as sodium percarbonate, a constituent (b) of this type is found to be more aggressive than is the case when constituent (b) contains component (ii). Therefore, constituent (b) which contains component (ii) alone is preferably used.

The preparation which is obtained by the method according to the present Invention can be used on the one hand for bleaching teeth and on the other hand for treating skin complaints and mucous membrane disorders.

For bleaching vital teeth; bleaching can be effected in the following way. First of all a sleeve or cap is made which has a shape which complements that of the visible part of the tooth to be bleached. In this context a complementary shape is understood to be a shape whereby the faces of the inside of the shape are essentially or completely identical to, and spatially assume approximately or precisely the same position as, the faces of the outside of the tooth to be bleached, so that when the sleeve or cap is fitted on the tooth a virtually abutting whole is obtained, the spacing or gap between the inside of the sleeve or cap and the tooth being approximately 0.01–5 mm, preferably 0.1–1 mm, and the cap or sleeve essentially or completely isolating at least the visible part of the tooth to be bleached from its surroundings. In this context the isolation obtained is such that the preparation is not able, or is barely able, to pass freely into the oral cavity. The preparation is then applied to the inside of the sleeve or cap, after which the sleeve or cap filled with the preparation is placed on the outside of the tooth. The sleeve or cap then remains in place for at least 6 hours, preferably 9 hours. At the end of this period, the covering is removed and the mouth is rinsed out well several times with copious amounts of water. The teeth are then cleaned thoroughly by brushing and by using dental floss and/or toothpicks and/or brushy tooth cleaners.

The method for bleaching a vital tooth then comprises the following steps:

I) the production of a cap in a shape which is complementary to that of at least the visible part of the tooth to be bleached, II) application of the preparation to the inside of the cap, III) fitting of the cap, the preparation having been applied to the inside of the cap, on the outside of a tooth, the cap remaining in place for at least 6 hours, preferably 9 hours, and IV) removal of the cap from the tooth.

It will be clear to a person skilled in the art that the method described above can also be carried out in the following way:

I) production of a cap in a shape which is complementary to that of the visible part of the tooth to be bleached, II) application of the preparation to the outside of the tooth to be bleached, III) fitting of the cap on the outside of a tooth, It being possible for a quantity of the preparation to be applied to the Inside of the cap if desired, and the cap being left in place for at least 6 hours, preferably 9 hours, and IV) removal of the cap from the tooth.

It will be clear to a person skilled in the art that if the preparation has already been applied to the tooth to be bleached it will not be necessary, or will not be necessary in all cases, to apply a quantity of the preparation to the inside of the sleeve or cap. However, both methods described above can be used to obtain the desired result and are therefore also considered to be part of the invention.

If further bleaching of the tooth or of the teeth is desired, the method can be repeated without this giving rise to adverse effects. Even in the case of this vital bleaching, the bleached tooth under normal circumstances retains, for a long to very long period, the colour which has been obtained by bleaching.

The sleeve or cap which is used in the methods described above is produced from a material which is deformable after warming, such as thermoplastic materials. Preferably, a material, for example a non-toxic polysiloxane, is used which can be brought into the desired shape after the material has been submerged in hot water for some time. Materials of this type are known in the prior art and are widely used for the production of, for example, gum shields, which are often worn when playing a sport. The shape of the cap is, thus, such that, or can be adjusted such that, the cap essentially or completely isolates the visible part of the tooth to be bleached from Its surroundings.

It can be seen from electron micrographs of teeth which have been treated on the outside with the preparation according to the invention that the preparation has no harmful effects on the enamel of the tooth treated. Moreover, it is found that the preparation has no harmful effects on the gums, but that the viricidal and bactericidal action of the preparation has a beneficial effect on the gums.

According to the present invention, the preparation as described above can also be used to treat specific skin complaints and mucous membrane conditions, in particular lesions.

As far as is known, there are no medicaments available commercially which are completely effective for lesions such as, for example, are caused by the herpes simplex virus.

Surprisingly, however, it has been found that the preparation of the present invention effects complete healing of herpes simplex lesions. For this purpose, for example, a mixture of equal parts of constituent (a) and constituent (b) is applied approximately five times a day to the lesions. In the case of incipient herpes simplex lesions, it is found that these lesions have disappeared after about 5 days, whilst when the lesions are more than three days old, said lesions have already disappeared after about two days. No scars are visible after healing. Further effects of the preparation in question are that the lesions do not spread, or barely spread, and that they recur less frequently.

In the case of aphthae (white ulcers) in the mouth as well, the mixture of equal parts of constituent (a) and constituent (b), for example, is found to have a healing effect. For example, when the mixture of equal parts of constituent (a) and constituent (b) is applied to the aphthae about six times a day, complete healing already takes place after two days, without the formation of visible scars. Complete healing without the formation of scars can also be achieved in the case of a skin condition such as acne when, for example, the mixture of equal parts of constituent (a) and constituent (b) is applied about five times to the areas to be treated. Furthermore, for example, the mixture of equal parts of constituent (a) and constituent (b) is found to have an effective healing action on moulds on the skin and the mucous membrane and on warts. The preparation according to the invention can therefore be used for the treatment of herpes simplex lesions, aphthae, acne, eczema, moulds on the skin or the mucous membrane, warts, splits in the corners of the mouth and the lips, chickenpox or other lesions of microbial origin.

For bleaching avital teeth, a constituent (a), which comprises component (i), and a constituent (b), which comprises component (ii), are applied alternately and layer by layer in a cavity in a tooth. Constituent (b), which comprises component (ii), is prepared by slightly moistening component (ii). Constituent (a), which comprises component (i), is prepared by dissolving component (i) in water. Because both constituents are applied individually and layer by layer and the preparation which comprises component (ii) is slightly moistened, the bleaching agent which is obtained by combining the two constituents is applied with a delayed action.

For bleaching an avital tooth, the restorative work on the tooth to be treated is first removed. The cavity which is thus obtained is then subjected to a number of cleaning and pretreatment steps, such as are normally carried out before a restorative material for a tooth is applied. Constituent (a), which comprises component (i), and constituent (b), which comprises component (ii), are then applied in the cavity, individually and layer by layer. Finally, means are applied so that the cavity is isolated from its surroundings.

The method for bleaching an avital tooth then comprises the following steps:

a) treatment of a cavity in a tooth with an etchant,
b) treatment of the cavity with a cleaning agent,
c) application of at least one layer of a constituent which comprises component (i). and at least one layer of a constituent which comprises component (ii), individually and layer by layer and
d) application of means which isolate the cavity from its surroundings.

The method described above can be used on one or more teeth at the same time. When the preparation is used in accordance with the method described above, the bleaching action is complete in 3–6 weeks. If further bleaching of the tooth or teeth is desired, the method can be repeated without this giving rise to adverse effects. Under normal circumstances, the bleached tooth retains, for a long to very long period, the colour which has been obtained by bleaching.

The preparation according to the invention can also be used in veterinary medicine and in industrial bleaching processes, for example in bleaching processes for paper.

The preparation according to the invention can also be used in an antimicrobial toothpaste, in which case component (i) and component (ii) are present in low concentrations, for example 5% by weight. Said toothpaste then has both an antimicrobial action and a bleaching or tint-reinforcing action. According to the invention the preparation can also be used in spray bandages, dermatological shampoos, soaps, ointments and gels.

The present invention also relates to a reaction product or reaction products for bleaching teeth and for treating skin complaints and mucous membrane disorders, in particular lesions, which product(s) is/are obtained by combining component (i) and component (ii). The surprisingly good and lasting bleaching effect of a preferred preparation according to the invention is caused by a synergistic effect between component (i) and component (ii). It is found that the use of either component (i) or component (ii) on its own results in little or no bleaching of a treated tooth and that the said compounds cannot be effectively used on their own for the treatment of lesions. In contrast, the use of the combination of component (i) and component (ii) according to the methods of the invention has a bleaching effect which is better and, moreover, longer lasting than could be expected on the basis of the results obtained from the use of the individual compounds. This shows that the two compounds intensify the effects of one another in a surprising manner.

Although the nature of this synergistic effect described above is not known, it is assumed, without wishing to be tied or restricted to any specific theory, that the complex chemistry of perborates (or peroxyborates) is responsible for this. The properties of these compounds are described in detail in Gmelin "Handbuch der Anorganischen Chemie", Volume 28, Part 7 (1975), pp. 221–237. Thus, it is known that the structure of sodium perborate tetrahydrate can be better described by the formula $NaBO_2.H_2O_2.3H_2O$ than by the more frequently used formula $NaBO_3.4H_2O$. On the other hand, the crystal structure of sodium perborate tetrahydrate shows that the compound consists of dinuclear anions, the boron ions being linked by two peroxo bridges (M. A. Carrondo, A. C. Skapsi, Acta Cryst. B34 (1978) 3551). In this case a better formula would be $Na_2[(HO)_2B(O)_2B(OH)_2].6H_2O$.

Raman spectrometry on aqueous solutions of sodium perborate tetrahydrate has revealed that the following equilibria are probably established (C. J. Adams and I. E. Clark in Polyhedron 2 (1983) 673–675):

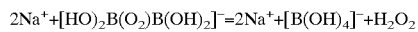

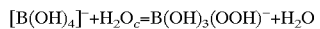

The position of these equilibria is found to be highly dependent on the prevailing pH. Moreover, in concentrated solutions $[B(OH)_4]^-$ can react further to give polyborates, as a result of which the description of these equilibria becomes appreciably more complex.

However, it has been found that $H_2O_2$ has a very moderate effect and has only a short-term action for the uses mentioned here. Because the preparation according to the invention has, specifically, an excellent and, moreover, lasting effect, it can be seen from this that the effect is not based on and/or caused by the formation of $H_2O_2$.

It is known that, depending on the conditions, sodium perborate tetrahydrate decomposes into sodium tetraborate, $Na_2B_4O_7$ and oxygen (Gmelin, "Handbuch der Anorganischen Chemie", Volume 28, Part 7 (1975), pp. 221–237). Although the conditions which prevail in the tooth (avital treatment) or in the oral cavity (vital treatment) are not known, it is assumed that oxygen is an active constituent of the bleaching agent. Moreover, it is found that when the preparation according to the invention is used in the oral cavity the patient does not experience the known stinging or burning sensation which is caused by $H_2O_2$. This could be explained by very slow or delayed formation of $H_2O_2$ and/or the formation of $H_2O_2$ in very small amounts, which is plausible because the preparation according to the invention contains only a very small amount of water.

According to Kirk-Othmer, "Encyclopedia of Chemical Technology", Part 13 (1981), page 15, $H_2O_2$ is capable of reducing relatively powerful oxidising agents such as hypochlorite. Because the preparation according to the invention can, for example, contain sodium hypochlorite, the latter would, in such a case, then be reduced to chloride and hydroxy anions, hydrogen peroxide decomposing to form oxygen and water. It therefore appears that the bleaching action of the preparation according to the invention is essentially caused by oxygen.

The surprisingly good and long-lasting effect of the preparation according to the invention thus appears not to lie in a combination of the normal bleaching mechanisms of component (i) and (ii) respectively, although it has not been established that these mechanisms have absolutely no significant role. The bleaching action of component (ii) such as, for example, sodium tetraborate usually takes place by epoxidation of unsaturated carbon-carbon bonds. It is thus also assumed that the bleaching action of component (i), such as, for example, sodium hypochlorite, normally takes place via a so-called hypohalite reaction, in which addition of, for example, HOCl to the unsaturated carbon-carbon bond takes place and, in the case of addition of HOCl, a so-called chlorohydrin is formed. However, it appears more probable that oxygen plays a significant role in the bleaching action of the preparation of the present invention, although a contribution by the other compounds mentioned above to the bleaching action is not precluded.

The invention is explained in more detail below with the aid of two examples of a method for bleaching, respectively, avital and vital teeth, an example of a method for treating lesions caused by the herpes simplex virus, and several examples providing methods for the preparation of dental and cosmetic products containing the preparation of this invention.

EXAMPLE I

This example describes a method for bleaching an avital tooth.

A X-ray photograph is first taken to establish whether the tooth to be bleached has been subjected to an endodontic treatment. An assessment must then be made as to whether the canal is properly closed off, at least as far as can be assessed from the photograph. If this is not the case, an endodontic treatment is carried out at this point.

The palatal or occlusal filling, which is present in the pulp cavity, and part of the canal filling are then successively removed. A measurement is taken using a pocket probe to determine whether the canal filling has been removed down to at least 2 mm below the buccal gingiva level. Using, for example, a thin endodontic file, a check is then carried out to determine whether the canal filling is sealing off the root canal properly.

The enamel and dentine inside the prepared hole in the tooth is etched for 10–60 seconds with 37% orthophosphoric acid, after which the hole is rinsed for 10 seconds with water in order to remove the etchant. The dentine inside the tooth is then treated for 10–60 seconds with a 20% EDTA solution in water, after which the hole is again rinsed for 10 seconds with water. The tooth is then blown dry. The bleaching agent is applied in layers in the following way. A layer of a preparation of sodium perborate and water is first applied at the deepest point of the cavity. The powder is compressed a little with the aid of a cotton wool ball. A cotton wool ball prepared with sodium hypochlorite and water is then taken. This cotton wool ball is pushed into the cavity on top of the preparation of sodium perborate and water. These latter steps are repeated several times, so that a layered build-up of the bleaching preparation is produced. The final layer in the cavity must always be a cotton wool ball prepared with sodium hypochlorite. The cavity is then sealed off by effecting temporary restorative work. This temporary restoration must be finished off as regards occlusion and articulation.

EXAMPLE II

This example describes a method for bleaching a vital tooth.

Two constituents (a) and (b) having the following compositions are prepared:

Constituent (a):
5 ml 4% sodium hypochlorite in water
2 mg sodium citrate
4 mg sodium fluoride (0.4% solution in water)
4 mg sodium carboxymethylcellulose
2.5 ml glycerol
2.5 ml 70% sorbitol in water Constituent (b):
3 g sodium perborate tetrahydrate
2 mg sodium citrate
4 mg sodium carboxymethylcellulose
5 ml glycerol 5 ml 70% sorbitol in water
2 mg magnesium sulphate or sodium sulphate The constituents (a) and (b) are preferably mixed as follows. Glycerol and sodium carboxymethylcellulose are mixed first and sorbitol is then mixed in. The other components can then be added in any order. If desired, the entire mixture can be heated briefly to about 100° C. during mixing, as a result of which more homogenous mixtures are obtained. To simplify processability, the two constituents (a) and (b) can be introduced into a so-called duo syringe.

Prior to the bleaching treatment, the tooth is cleaned thoroughly by brushing and by using dental floss and/or toothpicks and/or brushy tooth cleaners. The preparation is then prepared by placing equal amounts of constituents (a) and (b) in a mixing tray, after which the two constituents are mixed for 10 seconds with the aid of a spatula. The mixture obtained is applied to the inside of a silicone sleeve, which has previously been made to size, in such a way that the cheek side of the tooth to be bleached or of the teeth to be bleached comes into contact with the preparation when the silicone sleeve is fitted on the tooth. Excess preparation is removed. The silicone sleeve must preferably remain in place for at least 8 hours. Subsequently, the silicone sleeve is removed and the mouth is rinsed thoroughly several times with copious amounts of water. As the final step, the tooth is cleaned thoroughly again by brushing and by using dental floss and/or toothpicks and/or brushy tooth cleaners.

EXAMPLE III

A preparation containing equal amounts of constituent (a) and constituent (b) is prepared. The preparation is then applied, by smearing, to the affected tissue of a patient suffering from incipient herpes simplex lesions. The application is repeated about four times a day. The affected tissue is found to be completely healed within five days, whereas the lesions usually disappear only after 2–3 weeks.

The same results have been obtained with preparations which contain constituent (a) and constituent (b) in ratios of 10:1 to 1:10.

EXAMPLE IV

Antimicrobial tooth pastes were prepared as follows. First a preparation was prepared which contained equal amounts of constituents (a) and (b). Subsequently the antimicrobial tooth pastes were prepared containing 0.1 to 50% by weight of the preparation and 50 to 99.9% by weight of compositions used in tooth pastes, said compositions containing the usual constituents such as glycerol, water, silica xerogel, sodium laurylsulphate, hydroxyethylcellulose, sorbitol, sodium fluoride, flavourings and colourings.

EXAMPLE V

Dermatological shampoos were prepared as follows. First a preparation was prepared which contained equal amounts of constituents (a) and (b). Subsequently the dermatological shampoos were prepared containing 0.1 to 75% by weight of the preparation and 25 to 99.9% by weight of compositions used in shampoos, said compositions containing the usual constituents such as sodium laurylsulphate, lauric alcohol, sodium chloride, a alkanolamide of a fatty acid, EDTA, a conditioner and an anti-dandruff agent.

EXAMPLE VI

Spray bandages were prepared as follows. First a preparation was prepared which contained equal amounts of constituents (a) and (b). Subsequently the spray bandages were prepared containing 0.1 to 75% by weight of the preparation and 25 to 99.9% by weight of compositions used in spray bandages, said compositions containing the usual constituents such as acrylate and/or methacrylate, a solvent such as acetone, ethanol or ethyl acetate, derivatives of cellulose, a propellant such as pentane and/or butane and optionallly one or more antibiotics or antiseptics.

EXAMPLE VII

Dermatological soaps were prepared as follows. First a preparation was prepared which contained equal amounts of constituents (a) and (b). Subsequently the dermatological soaps were prepared containing 0.1 to 75% by weight of the preparation and 25 to 99.9% by weight of compositions used in soaps, said compositions containing the usual constituents such as sodium laurylethersulphate as used in soft soaps, or liquid or solid fatty acid based soaps.

I claim:

1. A combination preparation for bleaching teeth or for treating skin complaints and mucous membrane disorders comprising:
   (a) a gel or paste in which a component (i) is present, component (i) being composed of at least a cation $A^{n+}$ and an anion $O_m X^-$, wherein A is a metal from Group 1 or 2 of the periodic system, n=1 or 2, X is a halogen atom and m=1–4, and
   (b) gel or paste in which a component (ii) is present, component (ii) being composed of at least a cation $A^{n+}$ and an anion $[B_p O_q]^{r-}$, wherein A is a metal from Group 1 or 2 of the periodic system, p=1–4, q=1–8 and r=1–3.

2. Preparation according to claim 1, wherein A is lithium, sodium or potassium, n=m=p=1, q=2 or 3 and r=1–3.

3. Preparation according to claim 1, wherein X is chlorine.

4. Preparation according to claim 2, wherein A is sodium.

5. Preparation according to claim 2, wherein q=3 and r=1.

6. Preparation according to claim 2, wherein component (i) is sodium hypochlorite and component (ii) is sodium perborate.

7. Preparation according to claim 1, wherein (a) and (b) contain at least one of the following components: (iii) a binder, (iv) a gelatinous thickener, (v) an agent which counteracts loss of moisture.

8. Preparation according to claim 7, wherein component (iii) is glycerol, glycol, propylene glycol or a gum.

9. Preparation according to claim 7, wherein component (iv) is a cellulose material.

10. Preparation according to claim 7, wherein component (v) is an alditol.

11. Preparation according to claim 8, wherein component (iii) is glycerol.

12. Preparation according to claim 9, wherein component (iv) is sodium carboxymethylcellulose.

13. Preparation according to claim 10, wherein component (v) is sorbitol.

14. Preparation according to claim 7, wherein (a) is prepared in accordance with the following steps:
   a) mixing components (iii) and component (iv),
   b) mixing the mixture obtained in step 1 with component (v), and
   c) mixing the mixture obtained in step 2 with component (i).

15. Preparation according to claim 7, wherein (b) is prepared in accordance with the following steps:
   a) mixing components (iii) and component (iv),
   b) mixing the mixture obtained in step 1 with component (v), and
   c) mixing the mixture obtained in step 2 with component (ii).

16. Preparation according to claim 1, wherein (a) contains 0.1–95% by weight of component (i) and (b) contains 0.1–95% by weight of component (ii).

17. Preparation according to claim 16, wherein (a) contains 1–50% by weight of component (i) and (b) contains 1–50% by weight of component (ii).

18. A combination preparation for bleaching teeth or for treating skin complaints and mucous membrane disorders obtainable by admixing (a) and (b) as defined in claim 1.

19. A method for preparing a combination preparation for bleaching teeth and for treating skin complaints and mucous membrane disorders wherein (a) and (b) as defined in claim 1 are combined.

20. Method according to claim 19, wherein (a) and (b) contain one or more of the following components: (iii) a binder, (iv) a gelatinous thickener, (v) an agent which counteracts loss of moisture.

21. Method according to claim 20, wherein (a) is prepared in accordance with the following steps:
   a) mixing component (iii) and component (iv),
   b) mixing the mixture obtained in step 1 with component (v), and
   c) mixing the mixture obtained in step 2 with component (i).

22. Method according to claim 20, wherein (b) is prepared in accordance with the following steps:
   a) mixing component (iii) and component (iv),
   b) mixing the mixture obtained in step 1 with component (v), and
   c) mixing the mixture obtained in step 2 with component (ii).

23. A method for bleaching a vital tooth comprising:
   (a) producing a cap in a shape which is complementary to that of a least the visible part of the tooth to be bleached,
   (b) applying the combination preparation as defined in claim 18, to the inside of the cap,
   (c) fitting the cap, the preparation having been applied to the inside of the cap, on the outside of the tooth, the cap remaining in place for at least several hours, and
   (d) removing the cap from the tooth.

24. Method according to claim 23, wherein the cap remains in place for 9 hours.

25. Preparation according to claim 1, formulated for use as an active substance for bleaching teeth or for treating skin complaints and mucous membrane disorders.

26. Preparation according to claim 25, formulated for use as an active substance for bleaching vital teeth.

27. Preparation according to claim 25, formulated for use as an active substance for treating lesions.

28. Preparation according to claim 27, wherein the lesions are caused by the herpes simplex virus.

29. Preparation according to claim 25, formulated for use as an active substance for treating aphthae, acne, eczema, molds on the skin or the mucous membrane, warts, splits in the corners of the mouth and the lips, chickenpox or other lesions of microbial origin.

30. A method for treating lesions wherein a mixture of equal parts of (a) and (b) as defined in claim 1, is applied to lesions about five times a day.

31. Method according to claim 30, wherein the lesions are caused by the herpes simplex virus.

32. Method for treating aphthae in the mouth wherein a mixture of equal parts of (a) and (b) as defined in claim 1, is applied to aphthae in the mouth about six times a day.

33. The preparation according to claim 1 in antimicrobial toothpastes, spray bandages, dermatological shampoos, soaps, ointments or gels.

34. Kit-of-parts containing (a) and (b) as defined in claim 1, configured as a combined preparation for bleaching teeth or for treating skin complaints and mucous membrane disorders.

35. Kit-of-parts according to claim 34, containing (a) and (b) in separate containers.

36. Kit-of-parts according to claim 35 further comprising a cap or sleeve which can be formed in a shape complementary to that of at least the visible part of a tooth.

* * * * *